United States Patent
Guerra et al.

(10) Patent No.: US 11,984,212 B2
(45) Date of Patent: May 14, 2024

(54) SYSTEM FOR MONITORING DOSE PATTERN AND PATIENT RESPONSE

(71) Applicant: CareFusion 303, Inc., San Diego, CA (US)

(72) Inventors: Jesse J. Guerra, San Diego, CA (US); Prabhu Chinnaiah, San Diego, CA (US); Richard Wu, San Diego, CA (US)

(73) Assignee: CareFusion 303, Inc., San Diego, CA (US)

(*) Notice: Subject to any disclaimer, the term of this patent is extended or adjusted under 35 U.S.C. 154(b) by 707 days.

(21) Appl. No.: 16/739,389

(22) Filed: Jan. 10, 2020

(65) Prior Publication Data

US 2020/0222627 A1    Jul. 16, 2020

Related U.S. Application Data

(60) Provisional application No. 62/790,876, filed on Jan. 10, 2019.

(51) Int. Cl.
*G16H 20/17*    (2018.01)
*A61M 5/168*    (2006.01)
(Continued)

(52) U.S. Cl.
CPC ........ *G16H 20/17* (2018.01); *A61M 5/16831* (2013.01); *A61M 5/16854* (2013.01);
(Continued)

(58) Field of Classification Search
CPC .................................................. A61M 5/1723
See application file for complete search history.

(56) References Cited

U.S. PATENT DOCUMENTS 4,551,133 A * 11/1985 Zegers de Beyl .. A61M 5/1723
604/67
5,945,651 A   8/1999 Chorosinski et al.
(Continued)

FOREIGN PATENT DOCUMENTS

AU    2017 279 693 A1    1/2018
AU    2018335288 B2      8/2023
(Continued)

OTHER PUBLICATIONS

Qui et al. (2016) "A survey of machine learning for big data processing." *EURASIP Journal on Advances in Signal Processing*, Article No. 67, 16 pages.
(Continued)

*Primary Examiner* — Jenna Zhang
(74) *Attorney, Agent, or Firm* — Mintz Levin Cohn Ferris Glovsky and Popeo, P.C.

(57) ABSTRACT

A method for tracking dose pattern and patient response may include determining, based at least on one or more dose events at a pump configured to deliver a medication to a patient, a dose pattern for delivering the medication to the patient. One or more vital signs associated with the patient may be received from a patient monitor. A presence of one or more anomalies may be determined based at least on the dose pattern at the pump and the one or more vital signs of the patient. An electronic alert may be sent to a mobile device in response to determining the presence of the one or more anomalies. Related methods and articles of manufacture, including apparatuses and computer program products, are also disclosed.

17 Claims, 11 Drawing Sheets

(51) Int. Cl.
- *A61M 5/172* (2006.01)
- *G16H 40/63* (2018.01)
- *G16H 40/67* (2018.01)
- *G16H 50/20* (2018.01)
- *A61M 5/14* (2006.01)

(52) U.S. Cl.
CPC ...... *A61M 5/16877* (2013.01); *A61M 5/1723* (2013.01); *G16H 40/63* (2018.01); *G16H 40/67* (2018.01); *G16H 50/20* (2018.01); *A61M 2005/1405* (2013.01); *A61M 2205/18* (2013.01); *A61M 2205/3561* (2013.01); *A61M 2205/50* (2013.01); *A61M 2205/502* (2013.01); *A61M 2205/52* (2013.01); *A61M 2230/06* (2013.01); *A61M 2230/20* (2013.01); *A61M 2230/42* (2013.01); *A61M 2230/63* (2013.01)

(56) References Cited

U.S. PATENT DOCUMENTS

| | | |
|---|---|---|
| 5,961,036 A | 10/1999 | Michael et al. |
| 5,991,731 A | 11/1999 | Colon et al. |
| 6,650,964 B2 | 11/2003 | Spano, Jr. et al. |
| 6,671,579 B2 | 12/2003 | Spano, Jr. et al. |
| 6,842,736 B1 | 1/2005 | Brzozowski |
| 6,868,344 B1 | 3/2005 | Nelson |
| 7,119,689 B2 | 10/2006 | Mallett et al. |
| 7,184,897 B2 | 2/2007 | Nelson |
| 7,275,645 B2 | 10/2007 | Mallett et al. |
| 7,303,081 B2 | 12/2007 | Mallett et al. |
| 7,311,207 B2 | 12/2007 | Mallett et al. |
| 7,318,529 B2 | 1/2008 | Mallett et al. |
| 7,562,025 B2 | 7/2009 | Mallett et al. |
| 7,693,603 B2 | 4/2010 | Higham |
| 8,147,479 B1 | 4/2012 | Wach et al. |
| 8,195,328 B2 | 6/2012 | Mallett et al. |
| 8,280,550 B2 | 10/2012 | Levy et al. |
| 8,319,669 B2 | 11/2012 | Weller |
| 8,357,114 B2 | 1/2013 | Poutiatine et al. |
| 8,595,021 B2 | 11/2013 | Mallett et al. |
| 8,606,596 B1 | 12/2013 | Bochenko et al. |
| 8,725,532 B1 | 5/2014 | Ringold |
| 8,738,177 B2 | 5/2014 | Van Ooyen et al. |
| 8,768,724 B2 | 7/2014 | Whiddon et al. |
| 8,905,964 B2 | 12/2014 | Poutiatine et al. |
| 9,158,892 B2 | 10/2015 | Levy et al. |
| 9,202,052 B1 | 12/2015 | Fang et al. |
| 9,227,025 B2 | 1/2016 | Butterfield et al. |
| 9,354,178 B2 | 5/2016 | Lee |
| 9,427,520 B2 | 8/2016 | Batch et al. |
| 9,456,958 B2 | 10/2016 | Reddy et al. |
| 9,523,635 B2 | 12/2016 | Tilden |
| 9,636,273 B1 | 5/2017 | Harris |
| 9,752,935 B2 | 9/2017 | Marquardt et al. |
| 9,796,526 B2 | 10/2017 | Smith et al. |
| 9,817,850 B2 | 11/2017 | Dubbels et al. |
| 9,836,485 B2 | 12/2017 | Dubbels et al. |
| 9,842,196 B2 | 12/2017 | Utech et al. |
| 9,881,129 B1 | 1/2018 | Cave |
| 9,958,324 B1 | 5/2018 | Marquardt et al. |
| 10,032,344 B2 | 7/2018 | Nelson et al. |
| 10,101,269 B2 | 10/2018 | Judge et al. |
| 10,187,288 B2 | 1/2019 | Parker et al. |
| 10,209,176 B2 | 2/2019 | Proskurowski et al. |
| 10,241,038 B2 | 3/2019 | Nishimura et al. |
| 10,249,153 B2 | 4/2019 | Nelson et al. |
| 10,309,832 B2 | 6/2019 | Marquardt et al. |
| 10,345,242 B2 | 7/2019 | Zhao et al. |
| 10,832,207 B2 | 11/2020 | Vahlberg et al. |
| 11,037,666 B1 | 6/2021 | Benoit et al. |
| 11,116,892 B2 | 9/2021 | Brady et al. |
| 11,147,914 B2 | 10/2021 | Estes |
| 11,481,739 B1 | 10/2022 | McKinzie |
| 2003/0158751 A1 | 8/2003 | Suresh et al. |
| 2007/0260487 A1 | 11/2007 | Bartfeld et al. |
| 2008/0059226 A1 | 3/2008 | Melker et al. |
| 2008/0082360 A1 | 4/2008 | Bailey et al. |
| 2008/0140715 A1 | 6/2008 | Hakos |
| 2008/0243055 A1 | 10/2008 | Fathallah et al. |
| 2008/0288430 A1 | 11/2008 | Friedlander et al. |
| 2008/0306796 A1 | 12/2008 | Zimmerman et al. |
| 2008/0319795 A1 | 12/2008 | Poteet et al. |
| 2009/0083231 A1 | 3/2009 | Eberholst et al. |
| 2009/0160646 A1 | 6/2009 | Mackenzie et al. |
| 2010/0169063 A1 | 7/2010 | Yudkovitch et al. |
| 2010/0213250 A1 | 8/2010 | Mallett et al. |
| 2011/0016110 A1 | 1/2011 | Egi et al. |
| 2011/0082440 A1* | 4/2011 | Kimmo ................ G16H 20/17 604/503 |
| 2011/0161108 A1 | 6/2011 | Miller et al. |
| 2012/0226447 A1 | 9/2012 | Nelson et al. |
| 2012/0265336 A1 | 10/2012 | Mallett et al. |
| 2012/0325330 A1 | 12/2012 | Prince et al. |
| 2013/0002429 A1 | 1/2013 | Johnson |
| 2013/0018356 A1 | 1/2013 | Prince et al. |
| 2013/0070090 A1 | 3/2013 | Bufalini et al. |
| 2013/0144254 A1 | 6/2013 | Amirouche et al. |
| 2013/0158705 A1 | 6/2013 | Levy et al. |
| 2013/0253291 A1 | 9/2013 | Dixon et al. |
| 2013/0253700 A1 | 9/2013 | Carson et al. |
| 2013/0262138 A1 | 10/2013 | Jaskela et al. |
| 2013/0282392 A1 | 10/2013 | Wurm |
| 2013/0325727 A1 | 12/2013 | MacDonell et al. |
| 2014/0074284 A1 | 3/2014 | Czaplewski et al. |
| 2014/0081652 A1 | 3/2014 | Klindworth |
| 2014/0149131 A1 | 5/2014 | Bear et al. |
| 2014/0249776 A1 | 9/2014 | King et al. |
| 2014/0277707 A1 | 9/2014 | Akdogan et al. |
| 2014/0375324 A1 | 12/2014 | Matsiev et al. |
| 2015/0038898 A1 | 2/2015 | Palmer et al. |
| 2015/0061832 A1 | 3/2015 | Pavlovic et al. |
| 2015/0081324 A1 | 3/2015 | Adjaoute |
| 2015/0109437 A1 | 4/2015 | Yang et al. |
| 2015/0161558 A1 | 6/2015 | Gitchell et al. |
| 2015/0221086 A1 | 8/2015 | Bertram |
| 2015/0272825 A1 | 10/2015 | Lim et al. |
| 2015/0286783 A1 | 10/2015 | Kumar et al. |
| 2015/0294079 A1 | 10/2015 | Bergougnan |
| 2015/0323369 A1 | 11/2015 | Marquardt |
| 2015/0339456 A1 | 11/2015 | Sprintz |
| 2015/0362350 A1 | 12/2015 | Miller et al. |
| 2016/0034274 A1 | 2/2016 | Diao et al. |
| 2016/0062371 A1 | 3/2016 | Davidian et al. |
| 2016/0117478 A1 | 4/2016 | Hanina et al. |
| 2016/0161705 A1 | 6/2016 | Marquardt et al. |
| 2016/0166766 A1 | 6/2016 | Schuster et al. |
| 2016/0259904 A1 | 9/2016 | Wilson |
| 2016/0259911 A1 | 9/2016 | Koester |
| 2016/0283691 A1 | 9/2016 | Ali |
| 2017/0017760 A1 | 1/2017 | Freese et al. |
| 2017/0032102 A1 | 2/2017 | Skoda |
| 2017/0076065 A1 | 3/2017 | Darr et al. |
| 2017/0083681 A1 | 3/2017 | Sprintz et al. |
| 2017/0103203 A1 | 4/2017 | Sharma et al. |
| 2017/0108480 A1 | 4/2017 | Clark et al. |
| 2017/0109480 A1 | 4/2017 | Vahlberg |
| 2017/0109497 A1 | 4/2017 | Tribble et al. |
| 2017/0120035 A1 | 5/2017 | Butterfield et al. |
| 2017/0199983 A1 | 7/2017 | Cano et al. |
| 2018/0028408 A1 | 2/2018 | Li et al. |
| 2018/0039736 A1 | 2/2018 | Williams |
| 2018/0046651 A1 | 2/2018 | Dubbels et al. |
| 2018/0157803 A1 | 6/2018 | Mirov |
| 2018/0165417 A1 | 6/2018 | Hall et al. |
| 2018/0192942 A1* | 7/2018 | Clark .................. A61B 5/1128 |
| 2018/0203978 A1* | 7/2018 | Basu .................... G16H 50/30 |
| 2018/0231415 A1 | 8/2018 | Marquardt et al. |
| 2018/0247703 A1 | 8/2018 | D'Amato |
| 2018/0259446 A1 | 9/2018 | Coffey et al. |
| 2018/0299375 A1 | 10/2018 | Young et al. |
| 2018/0330824 A1 | 11/2018 | Athey et al. |
| 2018/0365385 A1* | 12/2018 | Cooney ................ G16H 20/60 |
| 2018/0365386 A1 | 12/2018 | Vanderveen |

(56) References Cited

U.S. PATENT DOCUMENTS

| | | |
|---|---|---|
| 2019/0088354 A1 | 3/2019 | Yanowitz et al. |
| 2019/0117883 A1 | 4/2019 | Abrams et al. |
| 2019/0124118 A1 | 4/2019 | Swafford |
| 2019/0139638 A1 | 5/2019 | Keefe et al. |
| 2019/0180862 A1 | 6/2019 | Wisser et al. |
| 2019/0244699 A1 | 8/2019 | Loebig et al. |
| 2019/0247703 A1 | 8/2019 | Welde et al. |
| 2019/0341142 A1 | 11/2019 | Nag et al. |
| 2019/0355461 A1 | 11/2019 | Kumar et al. |
| 2020/0085686 A1 | 3/2020 | Aliakbarian et al. |
| 2020/0098474 A1 | 3/2020 | Vanderveen |
| 2020/0219611 A1 | 7/2020 | Nag et al. |
| 2020/0230316 A1 | 7/2020 | Guerra et al. |
| 2020/0312442 A1 | 10/2020 | Hairr et al. |
| 2020/0402632 A1 | 12/2020 | van Schelven et al. |
| 2021/0005324 A1 | 1/2021 | Bostic et al. |
| 2021/0133201 A1 | 5/2021 | Tribble et al. |
| 2021/0308385 A1 | 10/2021 | Nisha et al. |
| 2022/0093239 A1 | 3/2022 | Nag et al. |

FOREIGN PATENT DOCUMENTS

| | | |
|---|---|---|
| CA | 2636115 C | 6/2014 |
| CA | 2848274 C | 9/2016 |
| EP | 1 973 593 B1 | 4/2013 |
| EP | 1 593 076 B1 | 10/2019 |
| JP | 2016-517077 A | 6/2015 |
| KR | 10-2014-0129141 A | 11/2014 |
| WO | WO-2006/034367 A2 | 3/2006 |
| WO | WO-2010/058796 A1 | 5/2010 |
| WO | WO-2011/014517 A1 | 2/2011 |
| WO | WO-2011/039676 A2 | 4/2011 |
| WO | WO-2014/055925 A1 | 4/2014 |
| WO | WO-2015/187682 A1 | 12/2015 |
| WO | WO-2019/028004 A1 | 2/2019 |
| WO | WO-2019/031331 A1 | 2/2019 |
| WO | WO-2020/206154 A1 | 10/2020 |

OTHER PUBLICATIONS

Yang, J., McAuley, J.J., & Leskovec, J. (2013). "Community Detection in Networks with Node Attributes." 2013 IEEE 13th International Conference on Data Mining, 1151-1156.

Benjamin, X.C. et al. (2012). "Visual identification of medicine boxes using features matching." *IEEE International Conference on Virtual Environments Human-Computer Interfaces and Measurement Systems(VECIMS) Proceedings*, 43-47. Doi: 10.1109/VECIMS.2012.6273190.

Cakaloglu, T. (Nov. 1, 2017). "Medi-Deep: Deep control in a medication usage." *2017 IEEE International Conference of Bioinfomratice and Biomedicine(BIBM)*, 899-904. Doi: 10.1109/BIBM.2017.8217776.

Neuman, M.R. et al. (May 13, 2012), "Advances in Medical Devices and Medical Electronics," in Proceedings of the IEEE, vol. 100, No. Special Centennial Issue, pp. 1537-1550,doi: 10.1109/JPROC.2012.2190684.

Shishvan, O. Rajabi et al. (2018). "Machine Intelligence in Healthcare and Medical Cyber Physical Systems: A Survey." *IEEE Access*. vol. 6, 46419-46494. doi: 10.1109/ACCESS.2018.2866049.

Uniyal, D. et al. (Nov. 7, 2014), "Pervasive Healthcare—A Comprehensive Survey of Tools and Techniques," arXiv:1411.1821v1, 48 pages.

Yaniv, Z. et al. (Oct. 1, 2016). "The National Library of Medicine Pill Image Recognition Challenge: An Initial Report." *Oct. 2016 IEEE Applied Imagery Pattern Recognition Workshop, (AIPR)*, 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

\* cited by examiner

SYSTEM FOR MONITORING DOSE PATTERN AND PATIENT RESPONSE

CROSS-REFERENCE TO RELATED APPLICATIONS

The present application claims priority to U.S. Provisional Application No. 62/790,876, filed on Jan. 10, 2019, and titled "SYSTEM FOR MONITORING DOSE PATTERN AND PATIENT RESPONSE," the entirety of which is incorporated by reference herein.

TECHNICAL FIELD

The subject matter described herein relates generally to the dispensation of pharmaceuticals and more specifically to a tracking system for the delivery of medication.

BACKGROUND

Patient-controlled analgesia pumps may provide patients direct control over the delivery of some medications including, for example, opioid pain medications, which are otherwise administered in single doses by medical professionals via intramuscular injections or intravenous injection. A patient-controlled analgesia pump is a computerized pump that houses a reservoir of multiple doses of a medication and is connected directly to a patient's vein. The patient-controlled analgesia pump may be configured to deliver a constant flow of the medication to the patient. Alternatively and/or additionally, the patient-controlled analgesia pump may allow the patient to self-administer individual doses of the medication on an as-needed basis.

SUMMARY

Systems, methods, and articles of manufacture, including computer program products, are provided for tracking dose pattern at a patient-controlled analgesic pump and patient response. For example, the patient-controlled analgesic pump may be communicatively coupled with a tracking engine configured to track a quantity and/or frequency of attempts to trigger the delivery of a dose of medication, the delivery of a dose of medication to a patient, and/or the denial of the delivery of a dose of medication to a patient. The tracking engine may be further configured to track the patient's vital signs including, for example, respiratory rate, oxygen saturation, heart rate, pain level, motor movement, and/or the like. The tracking engine may determine a correlation between the dose pattern observed at the patient-controlled analgesic pump and the patient's response. Moreover, the tracking engine may generate electronic alerts when one or more anomalies are detected in the dose pattern observed at the patient-controlled analgesic pump and/or the patient's vital signs.

According to some aspects, a method may include determining, based at least on one or more dose events at a pump configured to deliver a medication to a patient, a dose pattern for delivering the medication to the patient. The method may also include receiving, from a patient monitor, one or more vital signs associated with the patient. The method may further include determining, based at least on the dose pattern at the pump and the one or more vital signs of the patient, a presence of one or more anomalies. The method may also include sending, to a mobile device, an electronic alert in response to determining the presence of the one or more anomalies.

In some aspects, the one or more dose events may include an attempt by the patient to trigger a delivery of a dose of the medication, the delivery of the dose of the medication, and/or a denial of the delivery of the dose of the medication.

In some aspects, the one or more vital signs include a respiratory rate, an oxygen saturation, a heart rate, a pain level, and/or a motor movement.

In some aspects, the method further includes adjusting, based at least on the dose pattern at the pump and/or the one or more vital signs of the patient, the dose pattern at the pump. In some aspects, the dose pattern is adjusted by at least modifying a quantity and/or frequency of one or more doses of medication delivered to and/or denied from the patient. In some aspects, the dose pattern is adjusted by at least modifying a duration of an active period, an inactive period, and/or a lockout period at the pump. In some aspects, the dose pattern is adjusted by at least modifying a maintenance dose at the pump.

In some aspects, the one or more anomalies may include a volume of the medication delivered to the patient being greater than a maximum threshold value or less than a minimum threshold value. In some aspects, the one or more anomalies include the one or more vital signs of the patient being greater than a maximum threshold value or less than a minimum threshold value.

In some aspects, the patient monitor includes one or more sensors configured to measure the one or more vital signs of the patient. The one or more sensors may include at least one motion sensor. The presence of the one or more anomalies may be determined based on motion data measured by the at least one motion sensor.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to the tracking of dose pattern and patient responses, it should be readily understood that such features are not intended to be limiting.

The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

A patient-controlled analgesic pump may allow a patient to directly control the delivery of a medication instead of having to rely on medical professionals to administer the opioid pain medication via intramuscular injections or intravenous injections. For example, the patient-controlled analgesic pump may deliver, to the patient, one or more doses of the medication in response to the patient pressing a button on a handset coupled with the patient-controlled analgesic pump. To ensure timely, effective, and safe patient care, the use of patient-controlled analgesic pumps for delivering medication may still require frequent oversight from medical professionals. This may be especially true when a patient-controlled analgesic pump is being used to deliver controlled substances, such as opioid pain medications, that are susceptible to abuse and diversion and could cause adverse effects such as over sedation and low respiratory rate, loss of motor function, and/or apnea. As such, in some example embodiments, a tracking engine may be configured to track the doses of a medication delivered to and/or denied from/for a patient and the corresponding responses (e.g., vital signs) from the patient. For instance, the tracking engine may track the quantity of doses of the medication that was attempted by, delivered to, and/or, denied for the patient, the rate at which the doses of the medication were attempted by, delivered to, and/or, denied for the patient, as well as the patient's vital signs including, for example, respiratory rate, oxygen saturation, heart rate, pain level, motor movement (e.g., leg movement), and/or the like.

Figure 1:
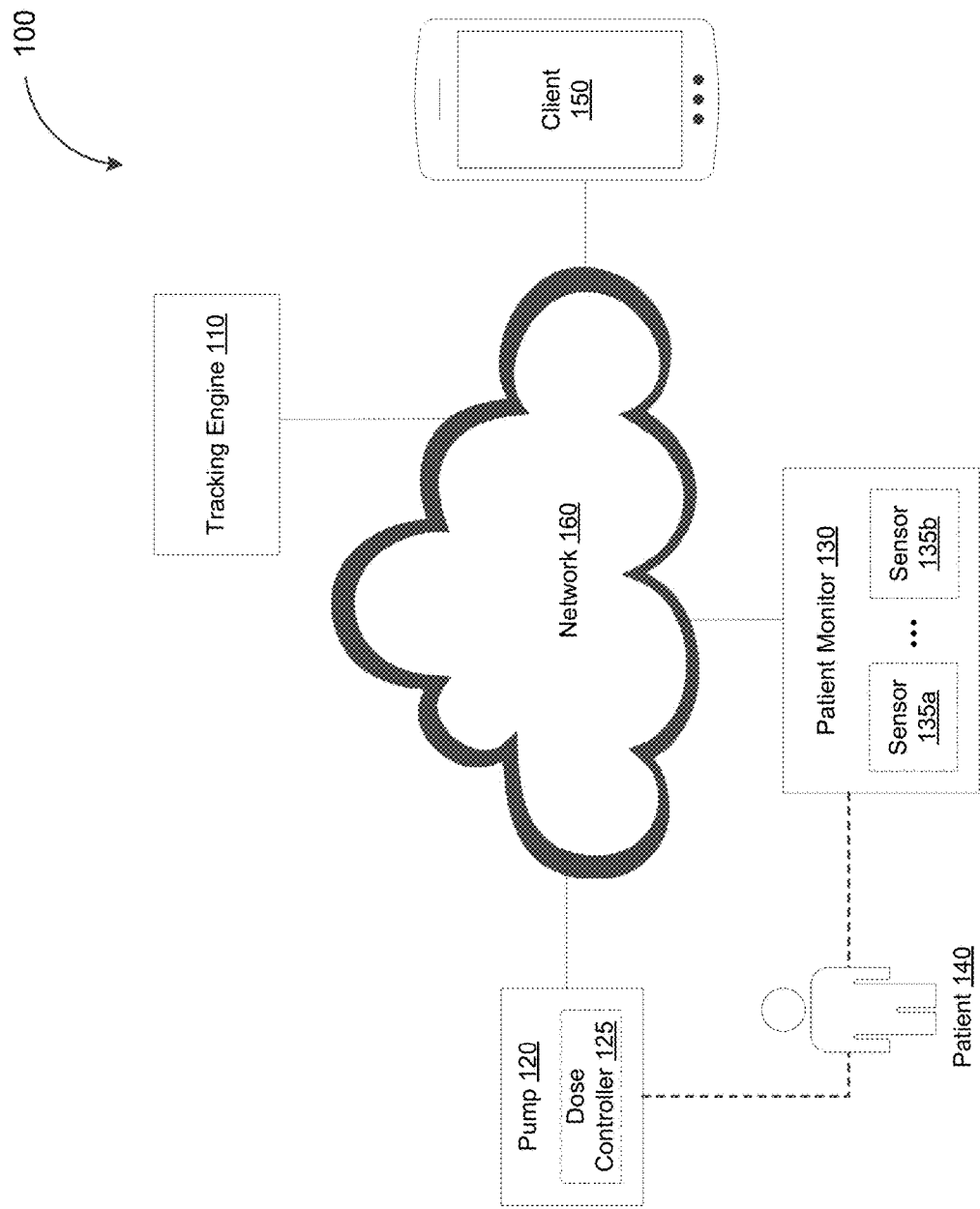
FIG. 1 depicts a system diagram illustrating a tracking system, in accordance with some example embodiments.

FIG. 1 depicts a system diagram illustrating a tracking system 100, in accordance with some example embodiments. Referring to FIG. 1, the tracking system 100 may include a tracking engine 110, a pump 120, a patient monitor 130, and a client 150. As FIG. 1 shows, the tracking engine 110, the pump 120, the patient monitor 130, and/or the client 150 may be communicatively coupled via a network 160. The client 150 may be a mobile device such as, for example, a smartphone, a tablet computer, a wearable apparatus, and/or the like. However, it should be appreciated that the client 150 may be any processor-based device including, for example, a desktop computer, a laptop computer, a workstation, and/or the like. Meanwhile, the network 160 may be any wired and/or wireless network including, for example, a public land mobile network (PLMN), a local area network (LAN), a virtual local area network (VLAN), a wide area network (WAN), the Internet, and/or the like. Additionally and/or alternatively, in some implementations, the tracking engine 110 and/or the client 150 may form a part of the pump 120.

The pump 120 may be a patient-controlled analgesic (PCA) pump configured to deliver a medication to a patient 140. However, it should be appreciated that the pump 120 may be any infusion system configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the infusion system may be configured to deliver a substance (e.g., fluid, nutrients, medication, and/or the like) to the patient's digestive system via a nasogastric tube (NG), a percutaneous endoscopic gastrostomy tube (PEG), a nasojejunal tube (NJ), and/or the like. The pump 120 may be configured to receive one or more syringes containing a medication such as, for example, an opioid pain medication (e.g., morphine, hydromorphone, fentanyl, and/or the like). Moreover, the pump 120 may deliver, to the patient 140, the medication in one or more doses including, for example, patient demand doses, clinician doses, loading doses, and/or maintenance doses. For instance, the patient 140 may trigger the delivery of a patient demand dose by at least pressing a button in a handset coupled with the pump 120. Additionally and/or alternatively, the patient-controlled analgesic pump may deliver, to the patient, one or more doses of the medication at set time intervals. In some implementations, the pump 120 may be used in an at-home setting, a clinical setting, in a convalescent care environment, and/or the like.

The pump 120 may include a dose controller 125 configured to detect one or more dose events at the pump 120 including, for example, the patient 140 attempting to trigger the delivery of a dose of medication, the delivery of a dose of medication to the patient 140, the denial of the delivery of a dose of medication to the patient 140, and/or the like. The dose controller 125 may report, to the tracking engine 110, the one or more dose events detected at the pump 120. In some example embodiments, the tracking engine 110 may determine, based at least on the one or more dose events reported by the dose controller 125, a dose pattern at the pump 120. For instance, the tracking engine 110 may determine a quantity and/or frequency of attempts to trigger the delivery of a dose of medication, the delivery of a dose of medication to the patient 140 (e.g., in response to an attempt to trigger the delivery of a dose of medication or at a set time interval), and/or the denial of the delivery of a dose of medication to the patient 140. As used herein, an attempt to trigger the delivery of a dose of medication may refer to a request by the patient 140 for the pump 120 to deliver a dose of medication, for example, by pressing a button on a handset coupled with the pump 120. Meanwhile, the denial of the delivery of a dose of medication may refer to the pump 120 preventing a dose of medication from being delivered to the patient 140 despite the patient 140 requesting the delivery of a dose of medication. The patient 140 may be denied the delivery of a dose of medication during a lockout period at the pump 120. For example, the delivery of one or more doses of medication to the patient 140 may trigger a subsequent lockout period at the pump 120 in order to prevent an excess of volume through frequency of the doses of medication from being delivered to the patient 140.

Referring again to FIG. 1, the patient monitor 130 may include one or more sensors including, for example, a first sensor 135a, a second sensor 135b, and/or the like. The first sensor 135a and/or the second sensor 135b may be wired and/or wireless sensors configured to measure one or more vital signs associated with the patient 140 including, for example, respiratory rate, oxygen saturation, carbon dioxide concentration, heart rate, pain level, motor movement (e.g., leg movement), rate of change of each vital sign, and/or the like. For example, at least one of the first sensor 135a and the second sensor 135b may be a motion sensor configured to detect the presence and/or absence of motor movement (e.g., from the lower extremities of the patient 140 as may the case when administering medication via an epidural space of the patient 140). As such, at least one of the first sensor 135a and the second sensor 135b may be positioned on or near a lower extremity of the patient 140, such as on the leg of the patient 140. Meanwhile, the patient monitor 130 may be configured to report, to the tracking engine 110, the one or more vital signs associated with the patient 140.

According to some example embodiments, the tracking engine 110 may be configured to track the one or more vital signs associated with the patient 140 along with the corresponding dose pattern observed at the pump 120. The tracking engine 110 may correlate the one or more vital signs associated with the patient 140 with the dose pattern observed at the pump 120. For example, the tracking engine 110 may determine the respiratory rate, oxygen saturation, carbon dioxide concentration, heart rate, motor movement, pain level, and/or rate of change of vital sign of the patient 140 when the patient 140 is subject to a certain dose pattern. As noted, the dose pattern observed at the pump 120 may include the quantity and/or frequency of attempts to trigger the delivery of a dose of medication, the delivery of a dose of medication to the patient 140, and/or the denial of the delivery of a dose of medication to the patient 140.

In some example embodiments, the tracking engine 110 may be configured to adjust, based on the dose pattern observed at the pump 120 and/or the vital signs of the patient 140 reported by the patient monitor 130, the dose pattern at the pump 120. The dose pattern at the pump 120 may be adjusted by at least modifying the quantity and/or frequency of the doses of medication delivered to the patient 140.

In some example embodiments, the tracking engine 110 may adjust the dose pattern at the pump 120 by at least changing a duration of an active period, an inactive period, and/or a lockout period at the pump 120. The active period may occur when the medication is being delivered to the patient 140. The inactive period may occur when the medication is not being delivered to the patient 140, but the medication is not prevented from being delivered to the patient 140 (e.g., during the lockout period). Increasing the duration of the active period at the pump 120 and/or decreasing the duration of the inactive period and/or lockout period at the pump 120 may result in an increase in the volume of medication delivered to the patient 140. Alternatively and/or additionally, the tracking engine 110 may adjust the dose pattern at the pump 120 by at least modifying a maintenance dose at the pump 120. For example, the tracking engine 110 may adjust the dose pattern at the pump 120 by adjusting the maximum dose limit associated with a given time period (e.g., one hour or a different time period) to increase or decrease the quantity of medication delivered to the patient during that time period. The tracking engine 110 may also adjust the dose pattern at the pump 120 by discontinuing the delivery of medication to the patient.

As used herein, a maintenance dose may refer to a minimum volume of medication administered continuously to the patient 140. Accordingly, modifying the maintenance dose at the pump 120 may trigger a corresponding change in the quantity and/or frequency of the doses of medication delivered to and/or denied from the patient 140.

In some example embodiments, the tracking engine 110 may also be configured to generate one or more electronic alerts based on the dose pattern observed at the pump 120 and/or the vital signs of the patient 140 reported by the patient monitor 130. The one or more electronic alerts may include wireless alert messages such as, for example, push notifications, short messaging service (SMS) message, and/or the like. Furthermore, the one or more electronic alerts may include an indication of a type of anomaly occurring in the dose pattern observed at the pump 120 and/or the vital signs of the patient 140 reported by the patient monitor 130. The anomaly may include, for example, end-tidal $CO_2$ (ETCO2) too high, no breath, low respiratory rate, quantity of denied patient demand doses exceeds limit, rate of change of vital sign exceeds a limit, a value of a vital sign exceeds a limit, high heart rate, quantity of patient demand doses with no or limited improvement in pain level, and/or the like. Alternatively and/or additionally, the one or more electronic alerts may include a patient identifier, a medication identifier, and/or a quantity of medication delivered to the patient. For instance, the one or more electronic alerts may specify the volume of medication, the quantity of doses, the rate of delivered doses, and/or the type of doses (e.g., patient demand doses, clinician doses, loading doses, maintenance doses, and/or the like) delivered to the patient.

For example, the tracking engine 110 may detect the presence of one or more anomalies in the dose pattern observed at the pump 120 and/or the vital signs of the patient 140 reported by the patient monitor 130. The one or more anomalies may include the volume of medication delivered to the patient 140 being greater than or equal to a maximum threshold value and/or less than or equal to a minimum threshold value. Alternatively and/or additionally, the one or more anomalies may include one or more vital signs of the patient 140 being greater than or equal to a maximum threshold value and/or less than or equal to a minimum threshold value. Alternatively and/or additionally, the one or more anomalies may include a rate of change in one or more vital signs of the patient 140 being greater than or equal to a maximum threshold value and/or less than or equal to a minimum threshold value. Alternatively and/or additionally, the one or more anomalies may include a quantity of medication delivered to the patient 140 with no or limited improvement in pain level being greater than or equal to a maximum threshold value and/or less than or equal to a minimum threshold value. The threshold values may be patient-specific (e.g., a predetermined value based on a number of factors, such as the patient's medical history, the patient's tolerance to certain types of medication, the patient's prior exposure to the medication and/or the like), and/or may be dynamically calculated depending on the dose pattern, patient vital signs, and/or the like. For example, the maximum and/or minimum threshold values may be greater if a patient has a medical history that includes a greater tolerance to certain types of medications, and/or prior exposure to the medication.

Figure 2A:
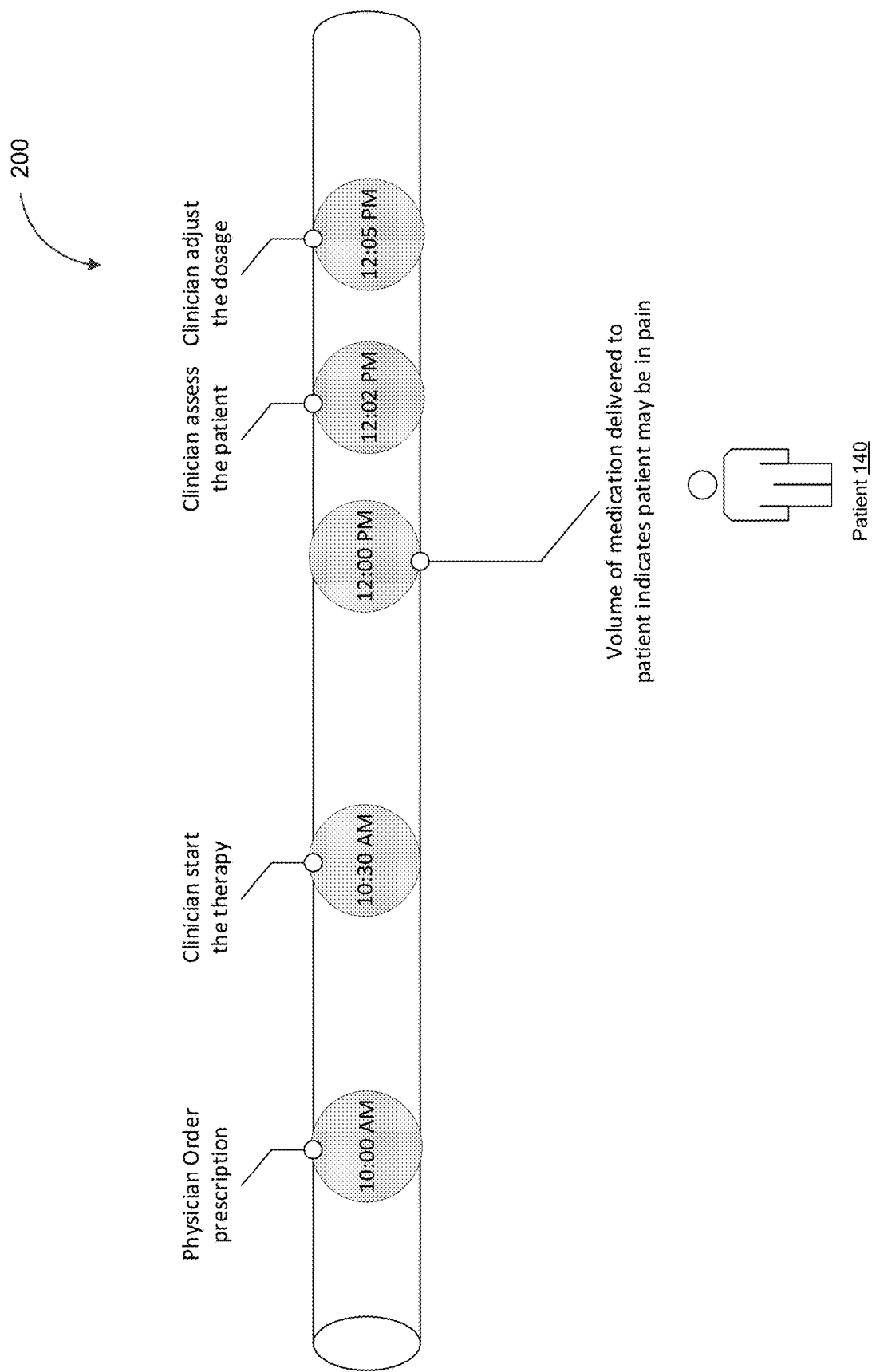
FIG. 2A depicts a sequence diagram illustrating the tracking of medication delivered to a patient and patient response, in accordance with some example embodiments.
Figure 2B:
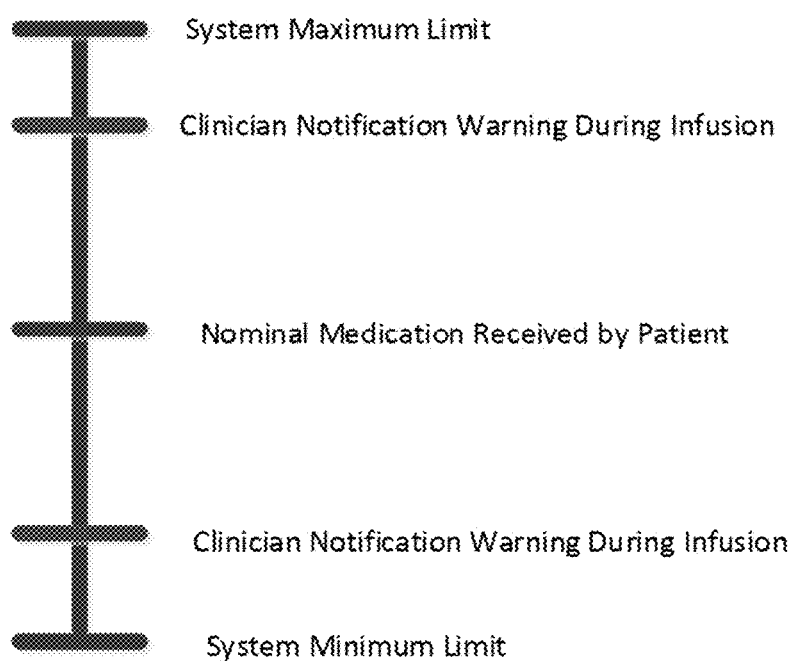
FIG. 2B depicts examples of alert thresholds associated with a tracking system, in accordance with some example embodiments.

To further illustrate, FIG. 2A depicts a sequence diagram 200 illustrating the tracking of medication delivered to a patient and patient response, in accordance with some example embodiments. Referring to FIGS. 1 and 2A, the tracking engine 110 may determine, based at least on the dose pattern observed at the pump 120, that the patient 140 is experiencing adverse symptoms (e.g., pain) at 12:00 PM. Alternatively and/or additionally, the tracking engine 110 may also determine, based at least on the one or more vital signs of the patient 140 reported by the patient monitor 130, that the patient 140 is experiencing adverse symptoms (e.g., pain, respiratory depression, apnea, decreased motor movement, and/or the like) at 12:00 PM. The tracking engine 110 may determine that the patient 140 is experiencing adverse symptoms at 12:00 PM based at least on the presence of one or more anomalies in the dose pattern observed at the pump 120 and/or the vital signs of the patient 140. As noted, the one or more anomalies may include the volume of medication delivered to the patient 140 being greater than a maximum threshold value and/or less than a minimum threshold value. In the example shown in FIG. 2A, the tracking engine 110 may determine that the patient 140 may be in pain based on the quantity of doses of medication being administered to the patient the pump 120. Alternatively and/or additionally, the one or more anomalies may include the vital signs of the patient 140 being greater than a maximum threshold value and/or less than a minimum threshold value. FIG. 2B depicts examples of alert thresholds associated with the tracking system 100, in accordance with some example embodiments.

For example, the tracking engine 110 may determine that the patient 140 is experiencing adverse symptoms at 12:00 PM based at least on the patient 140 attempting to trigger the delivery of one or more doses of medication from the pump 120. In response to determining that the patient 140 is experience adverse symptoms, the tracking engine 110 may be configured to adjust the dose pattern observed at the pump 120, for example, by modifying the quantity and/or frequency of the doses of medication delivered to the patient 140. Alternatively and/or additionally, the tracking engine 110 may respond to the patient 140 experiencing adverse symptoms by at least generating an electronic alert such as, for example, a push notification, a short messaging service (SMS) message, and/or the like. The electronic alert which may be sent to the client 150 associated with a medical professional in such that the medical professional may assess the patient 140 and/or adjust the dose pattern observed at the pump 120, for example, by modifying the quantity and/or frequency of the doses of medication delivered to the patient 140. The electronic alerts may be especially useful in some circumstances, such as when the patient 140 experiences no or limited improvement in pain level, even after the dose pattern is adjusted, and/or the patient continues to attempt to trigger the delivery of one or more doses of medication from the pump 120.

Figure 3A:
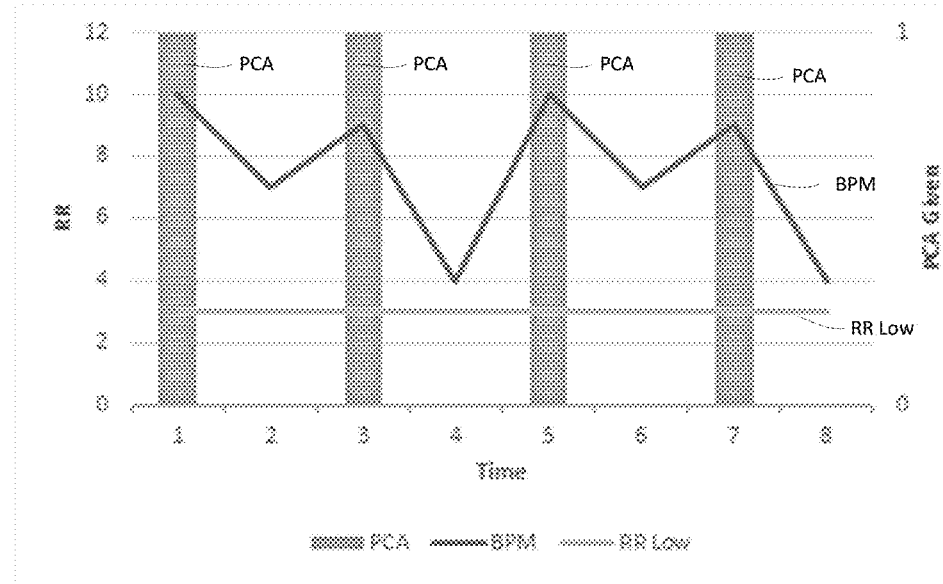
FIG. 3A depicts a graph illustrating a relationship between a frequency of doses administered to a patient and patient respiratory rate (BPM), in accordance with some example embodiments.
Figure 3B:
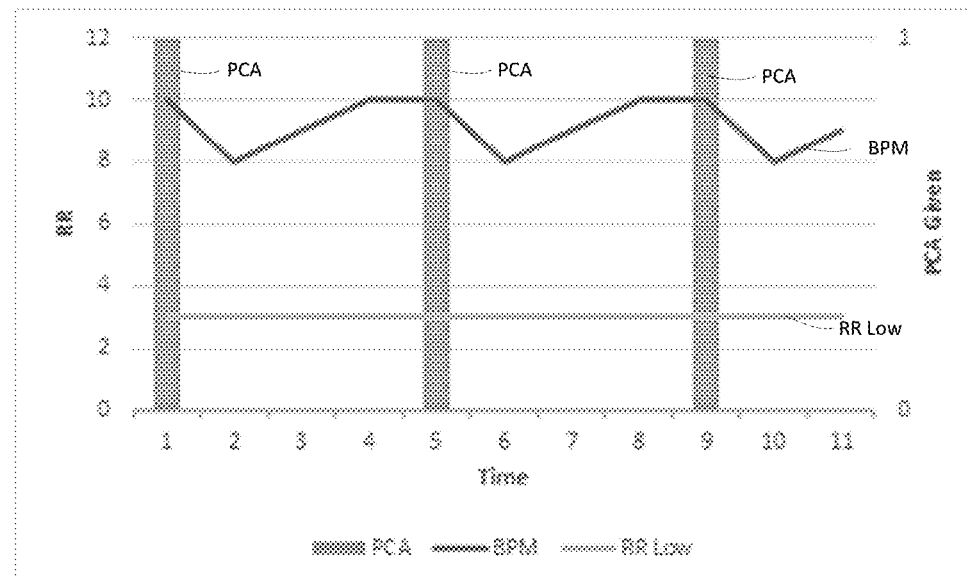
FIG. 3B depicts a graph illustrating a relationship between a frequency of doses administered to a patient and patient respiratory rate (BPM), in accordance with some example embodiments.

In some example embodiments, the tracking engine 110 may be configured to determine a correlation between the dose pattern observed at the pump 120 and the vital signs of the patient 140. To further illustrate, FIGS. 3A-D depict graphs illustrating the relationship between dose pattern and patient response. For example, the graphs shown in FIGS. 3A-B illustrate the relationship between a frequency of doses administered to the patient 140 and a respiratory rate of the patient 140. The quantity and/or frequency of doses of medication delivered to the patient 140 may affect the respiratory rate of the patient 140. For example FIG. 3A, illustrates four doses over seven units of time. FIG. 3A shows a gradual reduction in the detected beats per minute (BPM) which trends towards a respiratory rate threshold (RR Low). In FIG. 3B, the administration of three doses over eleven units of time maintains a higher BPM than shown in FIG. 3A.

Figure 3C:
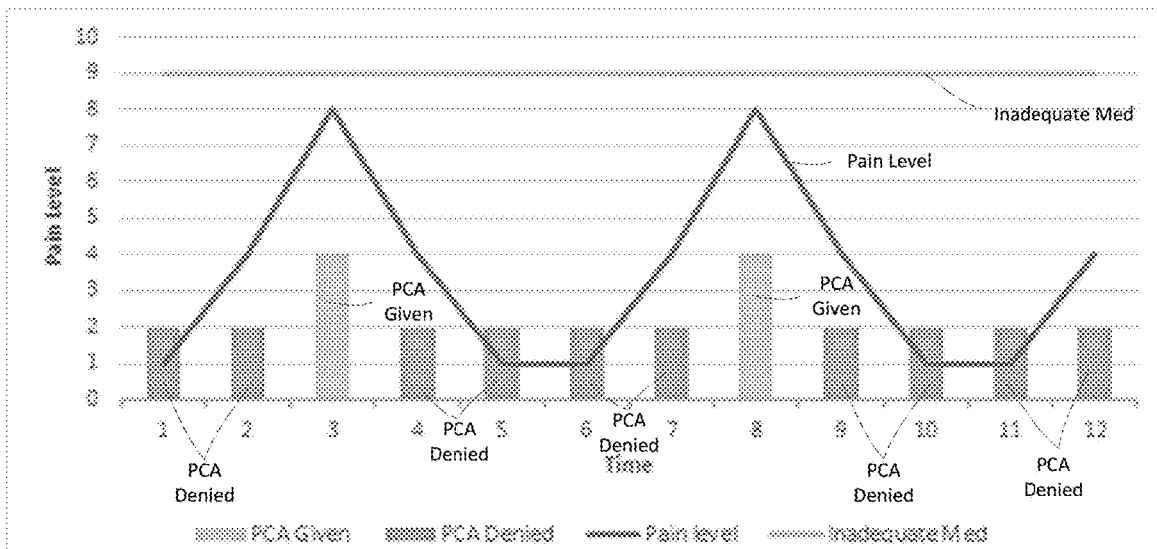
FIG. 3C depicts a graph illustrating a relationship between a frequency of doses denied to a patient and patient pain level, in accordance with some example embodiments.
Figure 3D:
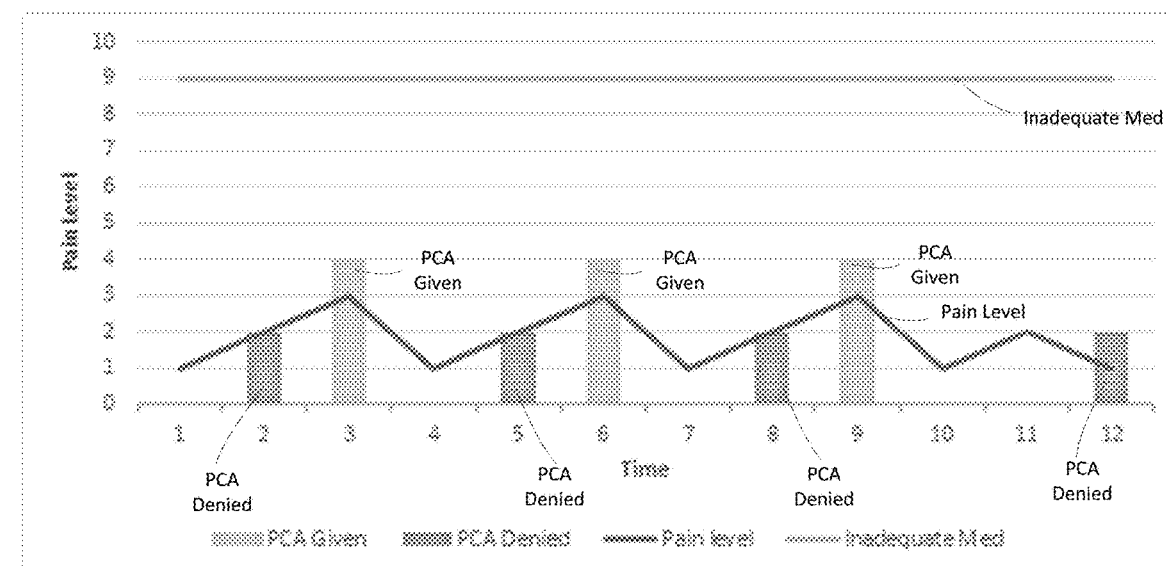
FIG. 3D depicts a graph illustrating a relationship between a frequency of doses denied to a patient and patient pain level, in accordance with some example embodiments.

Meanwhile, the graphs shown in FIGS. 3C-D illustrate the relationship between a frequency of doses denied to the patient 140 and a pain level of the patient 140. The quantity and/or frequency of doses of medication denied to the patient 140 may have an impact on the pain level and/or safety (e.g., over sedation, low respiratory rate and/or apnea) experienced by the patient 140. For instance, as shown in FIGS. 3C-D, the patient 140 may experience an increase in pain level when the patient 140 is denied delivery of medication by the pump 120. By contrast, the patient 140 may experience a decrease in pain level subsequent to the delivery of medication by the pump 120.

FIGS. 3C-D further illustrates that the pain level experienced by the patient 140 when the patient 140 is subject to different dose patterns. Referring to FIGS. 3C-D, the patient 140 may be denied delivery of medication more frequently with the dose pattern shown in FIG. 3C than with the dose pattern shown in FIG. 3D. For instance, over the same time period, the patient 140 may be provided with three doses of medication with the dose pattern shown in FIG. 3D but only two doses of medication with the dose pattern shown in FIG. 3C. Accordingly, with the dose pattern shown in FIG. 3C, the patient 140 may be given an insufficient quantity of medication because the pain level of the patient 140 spikes to a level (e.g., 8) that is close to the pain level indicative of inadequate medication (e.g., 9). By contrast, with the dose pattern shown in FIG. 3D, the pain level of the patient 140 remains relatively low (e.g., between 1 and 3) and does not approach the pain level associated with inadequate medication (e.g., 9).

Figure 3E:
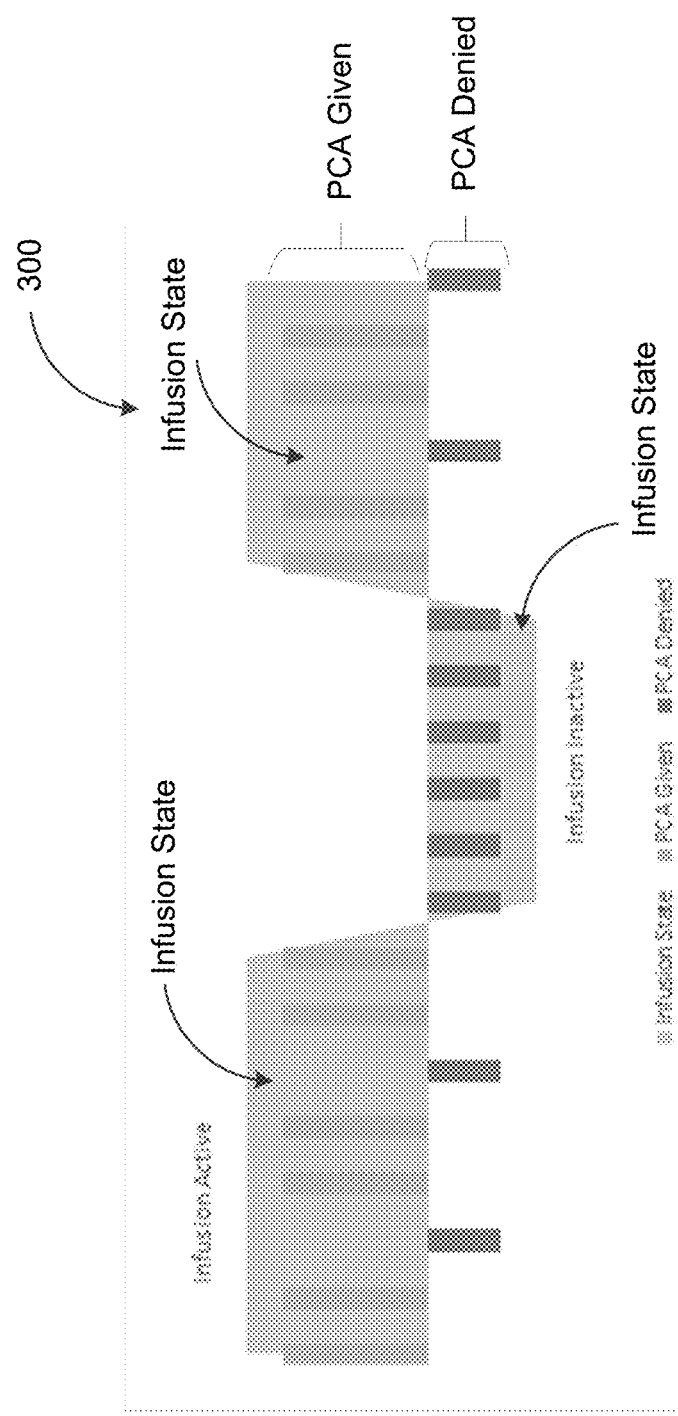
FIG. 3E depicts a graph illustrating an example of a dose pattern, in accordance with some example embodiments.

As noted, the patient 140 may be denied the delivery of a dose of medication during a lockout period at the pump 120. To prevent an excessive volume of medication (through frequency of doses being delivered) from being delivered to the patient 140, the pump 120 may undergo a lockout period subsequent to the delivery of one or more doses of medication to the patient 140. To further illustrate, FIG. 3E depicts a graph illustrating an example of a dose pattern 300, in accordance with some example embodiments. As shown in FIG. 3E, the pump 120 may be associated with an active state during which the pump 120 responds to at least some attempts from the patient 140 to trigger the delivery of a dose of medication by delivering, to the patient 140, a dose of medication. By contrast, while the pump 120 is in an inactive state, the pump 120 may deny all attempts from the patient 140 to trigger the delivery of a dose of medication. Moreover, FIG. 3E shows that the pump 120 may undergo a lockout period subsequent to every successful patient demand dose. For instance, after delivering a dose of medication to the patient 140 in response to a request from the patient 140, the pump 120 may undergo a lockout period during which any attempts by the patient 140 to trigger the delivery of another dose of medication may be denied.

Figure 4:
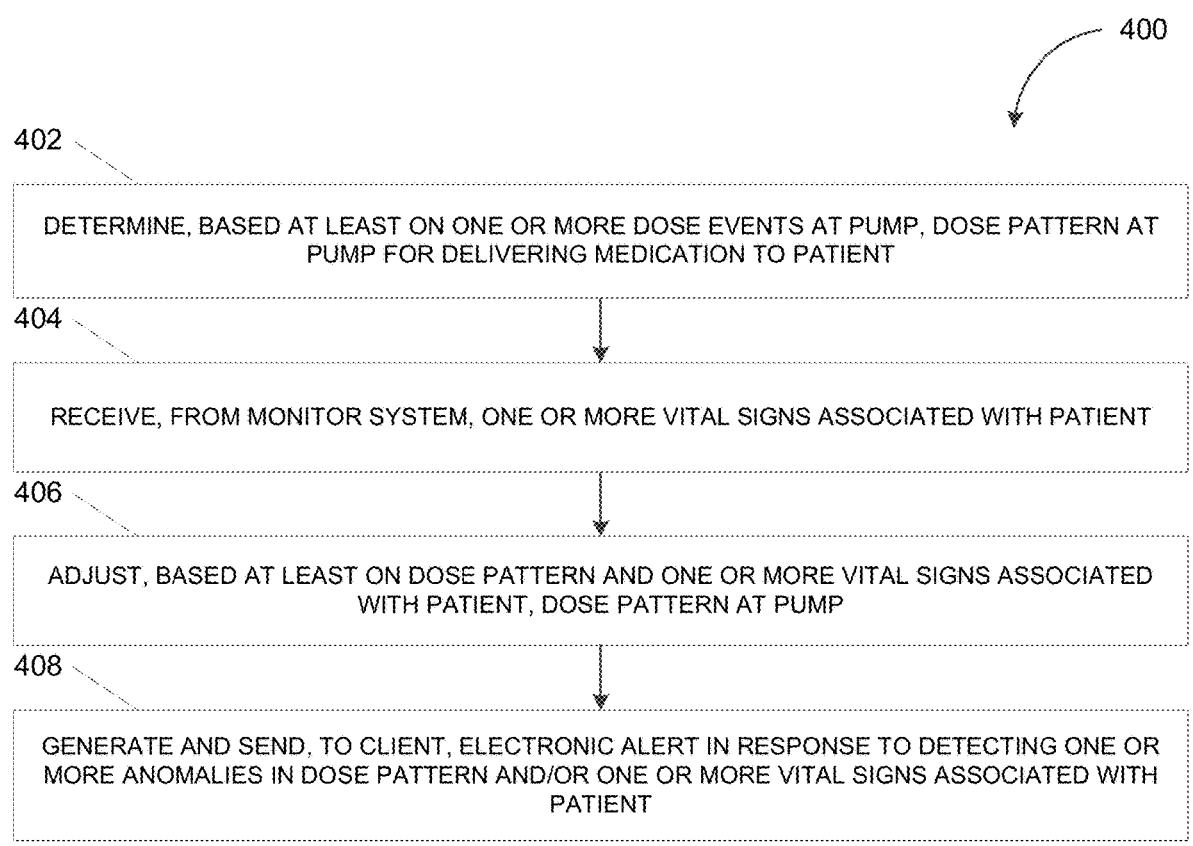
FIG. 4 depicts a flowchart illustrating a process for tracking medication delivered to a patient and patient response, in accordance with some example embodiments.

FIG. 4 depicts a flowchart illustrating a process 400 for tracking dose pattern and patient response, in accordance with some example embodiments. Referring to FIG. 4, the process 400 may be performed by the tracking system 100.

At 402, the tracking system 100 may determine, based at least on one or more dose events at the pump 120, a dose pattern at the pump 120 for delivering a medication to a patient. In some example embodiments, the dose controller 125 at the pump 120 may detect and report, to the tracking engine 110, one or more dose events at the pump 120 including, for example, the patient 140 attempting to trigger the delivery of a dose of medication, the delivery of a dose of medication to the patient 140, the denial of the delivery of a dose of medication to the patient 140, and/or the like. The tracking engine 110 may determine, based at least on the one or more dose events at the pump 120, a dose pattern at the pump 120 which may include, for example, a quantity and/or frequency of attempts to trigger the delivery of a dose of medication, the delivery of a dose of medication to the patient 140, and/or the denial of the delivery of a dose of medication to the patient 140.

At 404, the tracking system 100 may receive, from the patient monitor 130, one or more vital signs associated with the patient. In some example embodiments, the first sensor 135a and/or the second sensor 135b may be configured to measure and report, to the tracking engine 110, one or more vital signs associated with the patient 140 including, for example, respiratory rate, oxygen saturation, heart rate, pain level, motor movement, and/or the like.

At 406, the tracking engine 110 may adjust, based at least on the dose pattern at the pump 120 and the one or more vital signs associated with the patient, the dose pattern at the pump 120. In some example embodiments, the tracking engine 110 may be configured to adjust, based on the dose pattern observed at the pump 120 and/or the vital signs of the patient 140 reported by the patient monitor 130, the dose pattern at the pump 120. For example, the tracking engine 110 may adjust the dose pattern at the pump 120 by at least modifying the quantity and/or frequency of the doses of medication delivered to the patient 140. The quantity and/or frequency of the doses of medication delivered to and/or denied from the patient 140 may be modified by at least changing a duration of an active period, an inactive period, and/or lockout period implemented at the pump 120.

At 408, the tracking system 100 may generate and send, to the client 150, an electronic alert in response to detecting one or more anomalies in the dose pattern at the pump 120 and/or the one or more vital signs associated with the patient. In some example embodiments, the tracking engine 110 may be configured to track the one or more vital signs associated with the patient 140 along with the corresponding dose pattern observed at the pump 120. For example, the tracking engine 110 may correlate the one or more vital signs associated with the patient 140 with the dose pattern observed at the pump 120. Moreover, when the tracking engine 110 detect one or more anomalies in the dose pattern at the pump 120 and/or the one or more vital signs associated with the patient 140, the tracking engine 110 may generate and send, to the client 150 associated with a medical professional, an electronic alert (e.g., a push notification, a short messaging service (SMS) message, and/or the like). The one or more anomalies may include the volume of medication (e.g., dose of medication) delivered to the patient 140 being greater than a maximum threshold value and/or less than a minimum threshold value. Alternatively and/or additionally, the one or more anomalies may include one or more vital signs of the patient 140 being greater than a maximum threshold value and/or less than a minimum threshold value. The electronic alert may be sent to the client 150 such that the medical professional associated with the client 150 may assess the patient 140 and/or adjust the dose pattern observed at the pump 120, for example, by modifying the quantity and/or frequency of the doses of medication delivered to the patient 140.

Figure 5:
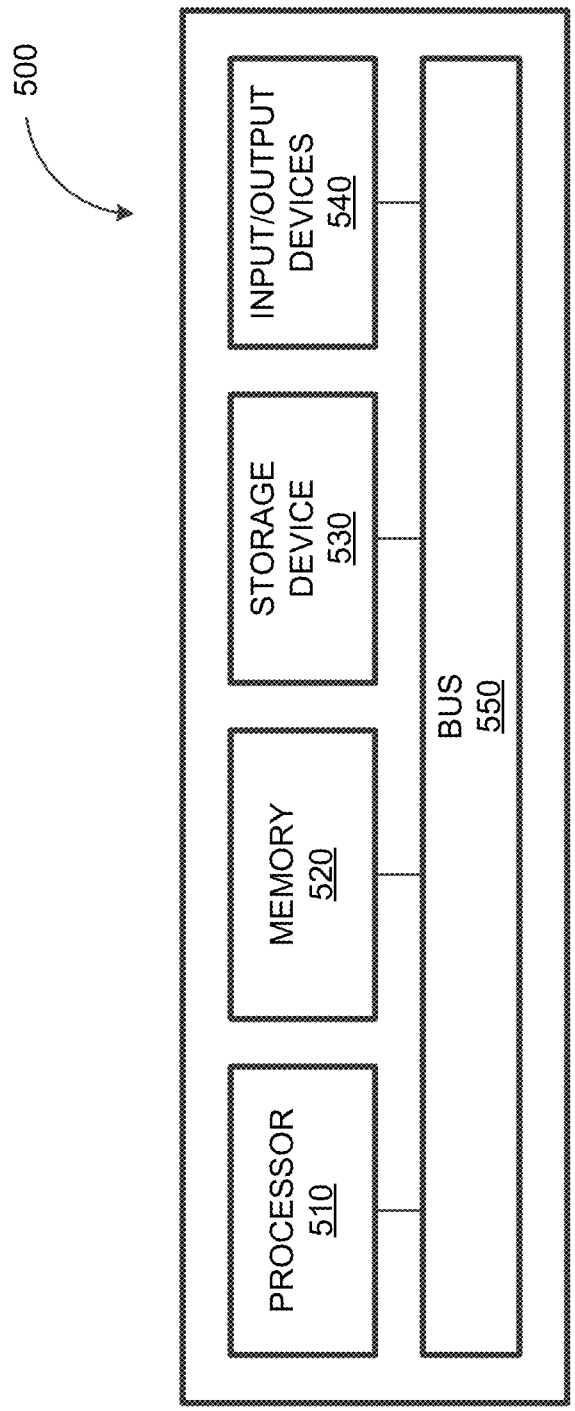
FIG. 5 depicts a block diagram illustrating a computing system, in accordance with some example embodiments.

FIG. 5 depicts a block diagram illustrating a computing system 500 consistent with implementations of the current subject matter. Referring to FIGS. 1 and 5, the computing system 500 can be used to implement the tracking engine 110 and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the tracking engine 110. In some example embodiments, the processor 510 can be a single-threaded processor. Alternatively, the processor 510 can be a multi-threaded processor. The processor 510 is capable of processing instructions stored in the memory 520 and/or on the storage device 530 to display graphical information for a user interface provided via the input/output device 540.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Figure 6A:
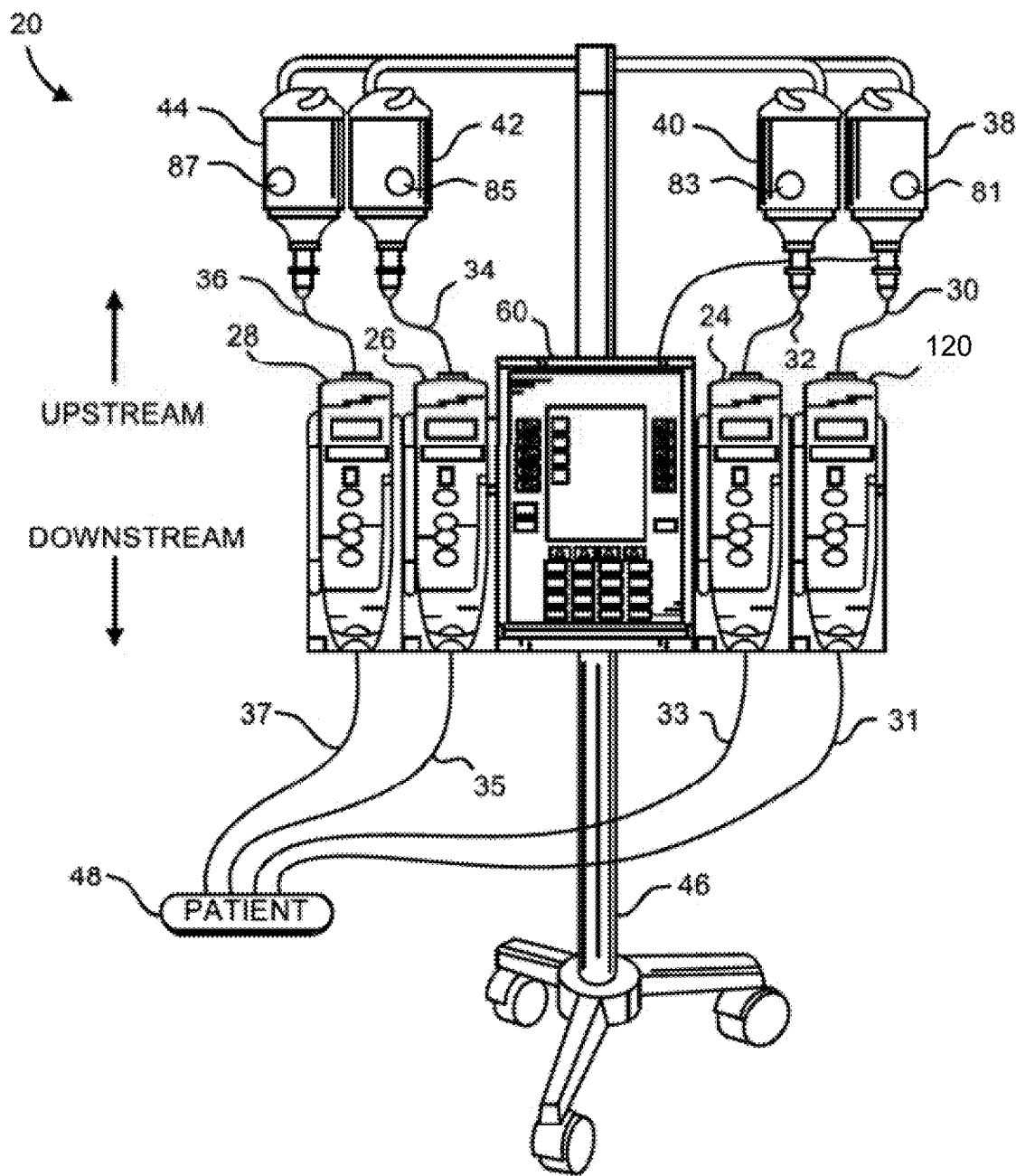
FIG. 6A depicts a front view of a patient care system, in accordance with some example embodiments.

In some example embodiments, the pump 120 may be part of a patient care system 20 shown in FIG. 6A. Referring to FIG. 6A, the patient care system 20 may include the pump 120 as well as additional pumps 24, 26, and 28. As shown in FIG. 6A, each of the pumps 120, 24, 26, and 28 may be fluidly connected with an upstream fluid line 30, 32, 34, and 36, respectively. Moreover, each of the four pumps 120, 24, 26, and 28 may also fluidly connected with a downstream fluid line 31, 33, 35, and 37, respectively. The fluid lines can be any type of fluid conduit, such as tubing, through which fluid can flow. At least a portion of one or more of the fluid lines may be constructed with a multi-layered configuration as described herein.

Fluid supplies 38, 40, 42, and 44, which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 are mounted to a roller stand or intravenous (IV) pole 46.

A separate pump 120, 24, 26, and 28 may be used to infuse each of the fluids of the fluid supplies into the patient. The pumps 120, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 6A. Many have check valves, drip chambers, valved ports, connectors, and other devices well known to those skilled in the art. These other devices have not been included in the drawings so as to preserve clarity of illustration. In addition, it should be noted that the drawing of FIG. 6A is not to scale and that distances have been compressed for the purpose of clarity. In an actual setting, the distance between the bottles 38, 40, 42, and 44 and the pumps 120, 24, 26, and 28 could be much greater.

Figure 6B:
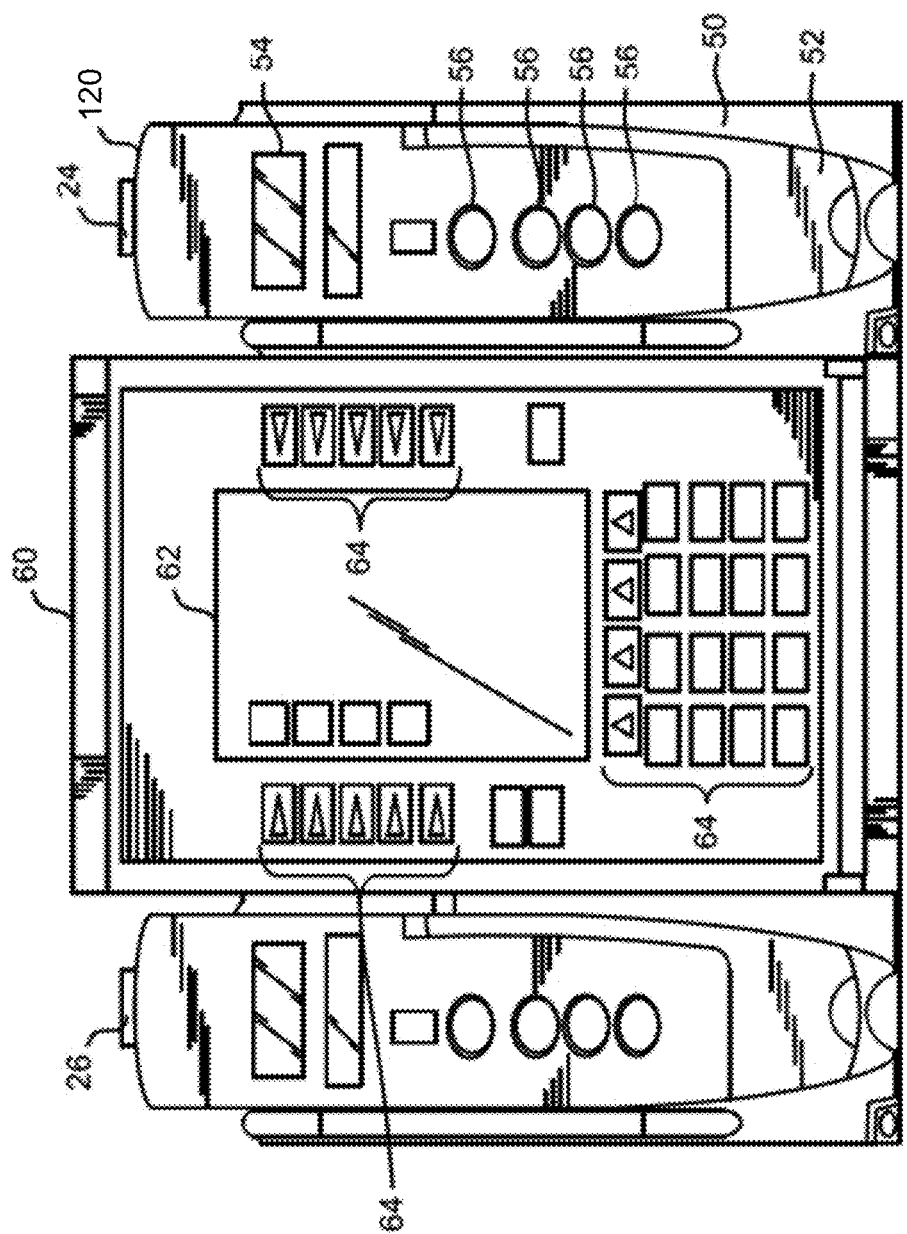
FIG. 6B depicts an enlarged view of a portion of a patient care system, in accordance with some example embodiments.

Referring now to FIG. 6B, an enlarged view of the front of the patient care system 20 is shown. The pump 120 may include a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 6C. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages) including the electronic alerts described herein (e.g., upon detection of one or more anomalies). Control keys 56 exist for programming and controlling operations of the pump as desired. The pump 120 also includes audio alarm equipment in the form of a speaker (not shown).

In the embodiment shown, a programming module 60 is attached to the left side of the pump 120. Other devices or modules, including another pump, may be attached to the right side of the pump 120, as shown in FIG. 6A. In such a system, each attached pump represents a pump channel of the overall patient care system 20. In one embodiment, the programming module is used to provide an interface between the pump 120 and external devices as well as to provide most of the operator interface for the pump 120.

The programming module 60 includes a display 62 for visually communicating various information, such as the operating parameters of the pump 120 and alert indications and alarm messages. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump. In some implementations, the pump 120 may provide data, such as the vital signs, to the programming module 60, which, in turn, may determine a dose pattern, detect one or more anomalies and/or cause transmission of electronic alerts associated with detected anomalies. In such implementations, the programming module 60 may communicate with the tracking engine 110, include the tracking engine 110, or implement features of the tracking engine 110 described herein.

The communications system may take the form of a radio frequency ("RF") (radio frequency) system, an optical system such as infrared, a Blue Tooth system, or other wired or wireless system. The bar code scanner and communications system may alternatively be included integrally with the pump 120, such as in cases where a programming module is not used, or in addition to one with the programming module. Further, information input devices need not be hard-wired to medical instruments, information may be transferred through a wireless connection as well.

FIG. 6B includes a second pump 26 connected to the programming module 60. As shown in FIG. 6A, more pump modules may be connected. Additionally, other types of modules may be connected to the pump modules or to the programming module. In such implementations, the tracking engine 110 may track a quantity and/or frequency of attempts to trigger the delivery of a dose of medication, the delivery of a dose of medication to a patient, and/or the denial of the delivery of a dose of medication to a patient at each pump (e.g., pump 120, pump 26, etc.). The tracking engine 110 may additionally and/or alternatively track the patient's vital signs at each pump (e.g., pump 120, pump 26, etc.). The tracking engine 110 may additionally and/or alternatively determine a correlation between the dose pattern observed at the patient-controlled analgesic pump and the patient's response at each pump (e.g., pump 120, pump 26, etc.). In some implementations, the tracking engine 110 may generate electronic alerts when one or more anomalies are detected in the dose pattern observed at each pump (e.g., pump 120, pump 26, etc.). The tracking engine 110 may provide additional or alternative control messages to adjust the function of one or more elements a pump based at least in part on the dose pattern detected. For example, the tracking engine 110 may disable a dispense button coupled to a patient controlled analgesic module. As another example, the tracking engine 110 may transmit a control message to adjust the rate of pumping by a motor (e.g., increase rate, decrease rate, or stop pumping). As another example, the tracking engine 110 may adjust a configuration for the pump such as the permitted dosing pattern (e.g., PCA lockout duration or frequency).

Figure 6C:
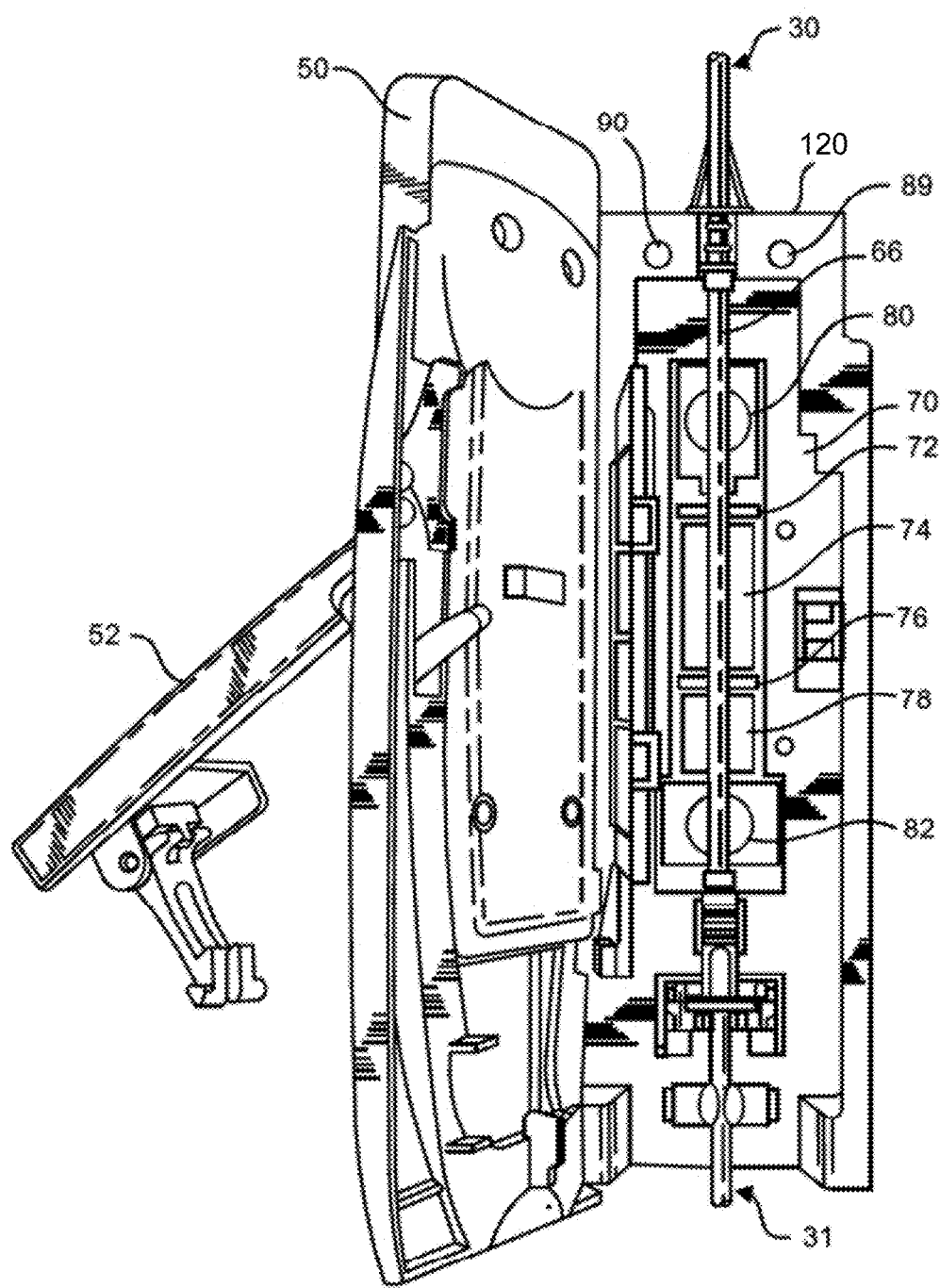
FIG. 6C depicts a perspective view of a pump, in accordance with some example embodiments.

Turning now to FIG. 6C, the pump 120 is shown in perspective view with the front door 50 open, showing the upstream fluid line 30 and downstream fluid line 31 in operative engagement with the pump 120. The pump 120 directly acts on a tube 66 (also referred to as a pump segment) that connects the upstream fluid line 30 to the downstream fluid line 31 to form a continuous fluid conduit, extending from the respective fluid supply 38 (FIG. 6A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 120, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 6C further shows a downstream pressure sensor 82 included in the pump 120 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 6A) and the flow control device, so that the connection of the correct fluid supply with the correct pump may be verified before any fluid is pumped to the patient.

With reference still to FIG. 6C, an upstream pressure sensor 80 may also be included in the pump 120. The upstream pressure sensor is assigned to the flow control device or pumping mechanism 70 and, in this embodiment, is further provided as an integral part of the pump 120. It is mounted to the flow control device 70 and is located adjacent and upstream in relation to the flow control device. The upstream pressure sensor is located upstream from the flow control device, that is, at a location between the fluid supply 38 (FIG. 6A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

Some implementations shown discuss features in relation to a pump. It will be understood that the features may be implemented in whole or in part using other medication dispensing devices such as an automated dispensing device, a robotically controlled delivery machine, or the like configured to provide medications or other substances for administration to a user.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data can be forwarded to a "remote" device or location," where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
   at least one data processor; and
   at least one memory storing instructions which, when executed by the at least one data processor, result in operations comprising:
      determining, based at least on one or more dose events at a pump configured to deliver a medication to a patient, a dose pattern for delivering the medication to the patient, wherein the dose pattern includes a quantity and a frequency of attempts to trigger a delivery of a dose of medication, the delivery of the dose of medication to the patient, and a denial of the delivery of the dose of medication to the patient;
      receiving, from a patient monitor, one or more vital signs associated with the patient;
      determining, based at least on the dose pattern at the pump and the one or more vital signs of the patient, a presence of one or more anomalies;
      sending, to a mobile device, an electronic alert in response to determining the presence of the one or more anomalies;
      determining an adjusted dose pattern based on the presence of the one or more anomalies; and
      causing administration of the medication to the patient according to the adjusted dose pattern.

2. The system of claim 1, wherein the instructions, when executed by the at least one data processor, result in further operations comprising triggering a lockout period at the pump to prevent an excess of volume through frequency of doses of medication from being delivered to the patient.

3. The system of claim 1, wherein the one or more vital signs include a respiratory rate, an oxygen saturation, a heart rate, a pain level, or a motor movement.

4. The system of claim 1, wherein the dose pattern is adjusted by at least modifying a quantity or frequency of one or more doses of medication delivered to or denied from the patient.

5. The system of claim 1, wherein the dose pattern is adjusted by at least modifying a duration of an active period, an inactive period, or a lockout period at the pump.

6. The system of claim 1, wherein the dose pattern is adjusted by at least modifying a maintenance dose at the pump.

7. The system of claim 1, wherein the one or more anomalies include at least one of a volume of the medication delivered to the patient being greater than a first maximum threshold value or less than a first minimum threshold value, and wherein the one or more vital signs of the patient being greater than a second maximum threshold value or less than a second minimum threshold value.

8. The system of claim 1, wherein the patient monitor includes one or more sensors configured to measure the one or more vital signs of the patient, wherein the one or more sensors include at least one motion sensor, and wherein the presence of the one or more anomalies is determined based on motion data measured by the at least one motion sensor.

9. A computer-implemented method, comprising:
   determining, based at least on one or more dose events at a pump configured to deliver a medication to a patient, a dose pattern for delivering the medication to the patient, wherein the dose pattern includes a quantity and a frequency of attempts to trigger a delivery of a dose of medication, the delivery of the dose of medication to the patient, and a denial of the delivery of the dose of medication to the patient;
   receiving, from a patient monitor, one or more vital signs associated with the patient; and
   determining, based at least on the dose pattern at the pump and the one or more vital signs of the patient, a presence of one or more anomalies; and
   sending, to a mobile device, an electronic alert in response to determining the presence of the one or more anomalies;
   determining an adjusted dose pattern based on the presence of the one or more anomalies; and
   causing administration of the medication to the patient according to the adjusted dose pattern.

10. The method of claim 9, further comprising triggering a lockout period at the pump to prevent an excess of volume through frequency of doses of medication from being delivered to the patient.

11. The method of claim 9, wherein the one or more vital signs include a respiratory rate, an oxygen saturation, a heart rate, a pain level, or a motor movement.

12. The method of claim 9, wherein the dose pattern is adjusted by at least modifying a quantity or frequency of one or more doses of medication delivered to the patient.

13. The method of claim 9, wherein the dose pattern is adjusted by at least modifying a duration of an active period, an inactive period, or a lockout period at the pump.

14. The method of claim 9, wherein the dose pattern is adjusted by at least modifying a maintenance dose at the pump.

15. The method of claim 9, wherein the one or more anomalies include at least one of a volume of the medication delivered to the patient being greater than a first maximum threshold value or less than a first minimum threshold value, and wherein the one or more anomalies include the one or more vital signs of the patient being greater than a second maximum threshold value or less than a second minimum threshold value.

16. A non-transitory computer-readable storage medium including program code, which when executed by at least one data processor, cause operations comprising:
   determining, based at least on one or more dose events at a pump configured to deliver a medication to a patient, a dose pattern for delivering the medication to the patient, wherein the dose pattern includes a quantity and a frequency of attempts to trigger a delivery of a dose of medication, the delivery of the dose of medication to the patient, and a denial of the delivery of the dose of medication to the patient;
   receiving, from a patient monitor, one or more vital signs associated with the patient; and
   determining, based at least on the dose pattern at the pump and the one or more vital signs of the patient, a presence of one or more anomalies;
   sending, to a mobile device, an electronic alert in response to determining the presence of the one or more anomalies;
   determining an adjusted dose pattern based on the presence of the one or more anomalies; and
   causing administration of the medication to the patient according to the adjusted dose pattern.

17. The system of claim 1, wherein the instructions, when executed by the at least one data processor, result in further operations comprising determining a correlation between the dose pattern observed at the pump and the one or more vital signs of the patient.

* * * * *